US 8,497,370 B2
Jul. 30, 2013

(12) United States Patent
Chen (54) PROCESSES FOR PREPARING AMINE SALTS OF SILDENAFIL-ANALOGUES AND USE THEREOF

(75) Inventor: Ing-Jun Chen, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 97 days.

This patent is subject to a terminal disclaimer.

(21) Appl. No.: 13/044,899

(22) Filed: Mar. 10, 2011

(65) Prior Publication Data

US 2012/0108604 A1    May 3, 2012

(30) Foreign Application Priority Data

Nov. 2, 2010 (TW) ............................... 99137696 A (51) Int. Cl.
C07D 473/00 (2006.01)
A61K 31/497 (2006.01)
C08B 15/06 (2006.01)

(52) U.S. Cl.
USPC ......... 544/270; 544/262; 514/252.16; 536/31

(58) Field of Classification Search
USPC .................. 514/252.16; 544/270; 536/31
See application file for complete search history.

(56) References Cited

U.S. PATENT DOCUMENTS

| | | | |
|---|---|---|---|
| 4,231,938 A | 11/1980 | Monaghan et al. | |
| 4,346,227 A | 8/1982 | Terahara et al. | |
| 4,444,784 A | 4/1984 | Hoffman et al. | |
| 4,681,893 A | 7/1987 | Roth | |
| 4,739,073 A | 4/1988 | Kathawala | |
| 5,006,530 A | 4/1991 | Angerbauer et al. | |
| 5,159,104 A | 10/1992 | Dabora et al. | |
| 5,177,080 A | 1/1993 | Angerbauer et al. | |
| 5,260,440 A | 11/1993 | Hirai et al. | |
| 5,273,995 A | 12/1993 | Roth | |
| 5,298,627 A | 3/1994 | Butler et al. | |
| 5,358,941 A | 10/1994 | Bechard et al. | |
| 5,489,690 A | 2/1996 | Butler et al. | |
| 6,002,021 A | 12/1999 | Yang et al. | |
| 6,087,362 A | 7/2000 | El-Rashidy | |
| 6,100,407 A | 8/2000 | Van Dalen et al. | |
| 6,316,460 B1 | 11/2001 | Creekmore et al. | |
| 6,362,178 B1 | 3/2002 | Niewöhner et al. | |
| 7,618,976 B2 | 11/2009 | Braude et al. | |
| 8,268,847 B2* | 9/2012 | Clozel | 514/269 |
| 2005/0085486 A1 | 4/2005 | Gonzalez-Cadavid et al. | |
| 2008/0312249 A1 | 12/2008 | Chen | |
| 2009/0318459 A1* | 12/2009 | Clozel | 514/250 |
| 2010/0317671 A1* | 12/2010 | Chen | 514/252.16 |

FOREIGN PATENT DOCUMENTS

| | | |
|---|---|---|
| EP | 1779852 | 5/2007 |
| EP | 2024369 | 12/2007 |
| WO | 9513283 | 5/1995 |
| WO | 9849166 | 11/1998 |

OTHER PUBLICATIONS

U.S. Appl. No. 12/878,451, filed Sep. 9, 2010, Ing-Jun Chen.
Lin et al., "KMUP-1 relaxes rabbit corpus cavernosum smooth muscle in vitro and in vivo: involvement of cyclic GMP and K+ channels," British Journal of Pharmacology (2002) 135, 1159-1166.
Wu et al., "KMUP-1, a xanthine derivative, induces relaxation of guinea-pig isolated trachea: the role of the epithelium, cyclic nucleotides and K+ channels," British Journal of Pharmacology (2004) 142, 1105-1114.
Office Action, Taiwanese Patent Application No. 099137696, issued Feb. 20, 2013.
Ying et al., "Effect of Zocor Simvastatin on Nitric Oxide and Endothelin in Kidney Damaged Rats Induced by Hyperlipidemia," Journal of Huazhong University of Science and Technology, Health Science, 2006, 35(3): 301-304. Abstract.
Zhao et al, "Simvastatin and sildenafil combine to attenuate pulmonary hypertension," European Respiratory Journal, 2009, 34: 948-957.

* cited by examiner

*Primary Examiner* — Shirley V Gembeh
(74) *Attorney, Agent, or Firm* — Volpe and Koenig, P.C.

(57) ABSTRACT

A series of amine salts including a structure of formula (I) and formula (III) have provided. In formula I or formula (III), $R_1$, $R_a$ and RX are as defined in the specification. The amine complex salts disclosed in the present invention are characterized in a pro-drug active form and various pharmaceutical function.

10 Claims, 2 Drawing Sheets

FIG.1

Sildenafil (1)

Homosildenafil (2)

Hydroxyhomosildenafil (3)

Desmethylsildenafil (4)

Acetidenafil (5)

Vardenafil (6)

Udenafil (7),

FIG.2

Sildenafil-Lovastatinic acid (8)

Sildenafil-Rosuvastatinic acid (9)

-Mevastatinic acid (10)

PROCESSES FOR PREPARING AMINE SALTS OF SILDENAFIL-ANALOGUES AND USE THEREOF

The application claims the benefit of Taiwan Patent Application No. 099137696, filed on Nov. 2, 2010, in the Taiwan Intellectual Property Office, the disclosures of which are incorporated by reference herein in their entirety.

FIELD OF THE INVENTION

The present invention relates to the amine complex salts and their preparation thereof used as the pro-drugs with different pharmaceutical functions.

BACKGROUND OF THE INVENTION

Pfizer's Sildenafil Citrate (registered trademark Viagra) possesses pharmacological mechanism to increase 3',5'-cyclic guanosine monophosphate (cGMP) through inhibiting phosphodiesterase (PDE). Prior studies directly proves that the role of cGMP and PKG-1 signaling could reveal suppression of ventricular hypertrophy. Clinical efficacy of Sildenafil Citrate is used in treatment of male sexual function and in improvement on pulmonary arterial hypertension (PAH), erectile dysfunction (ED), and urinary symptoms in men with benign prostatic hyperplasia (BPH) with lower urinary tract symptom (LUTS) or depression.

Although World Patent No. WO 9849166 A1 discloses that the synthesis method of Sildenafil, and the other with 2-pentanone and diethyl oxalate as raw material can be synthesized Sildenafil, such methods of synthesis are usually only based the pyrazolo[4,3d]pyrimidin-7-one moiety structure of Sildenafil compounds. The Sildenafil salt disclosed in these specification is the general type of pharmaceutically acceptable salt. Both EP 2024369 and EP 1779852, and U.S. Pat. No. 7,618,976 disclosed the synthesis method of Sildenafil Citrate. U.S. Pat. No. 6,087,362 disclosed the pharmaceutical composition which is oral administration of Apomorphine and Sildenafil, or Sildenafil and cyclodextrin.

The xanthine based derivative compound of KMUP-1 has indicated that its activity includes the activation of endothelial NOS (eNOS), associated activation of soluble guanylyl cyclase (sGC) and inhibition of phosphodiesterase-5A (a PDE-5A inhibitor). It is already proven that KMUP-1 can effect the cyclic adenosine monophosphate, (cAMP)/protein kinase A (PKA) and cGMP/PKG signaling pathways thereby activating sGC (Wu et al., 2004). KMUP-1 has been described to have not only induce eNOS release but also have the resembling NO donor effects. For many years study, the inventor has found that KMUP-1 compound has some pleiotropic activities. This invention relates to treating the hypertension as US APPLICATION No. US 20080312249, on the treatment of benign prostatic hyperplasia as No. US 20050085486, and treating pulmonary hypertension as US 20080312249.

SUMMARY OF THE INVENTION

Inventor had the idea of synthesizing KMUP compounds or piperazine salt for the preparation of quaternary piperazinium complex salts compound, represented by the following formula (I)

or formula (II).

As shown in the U.S. patent application Ser. No. 12/878,451, filed on 29 Jan. 2010, the performed synthesis of monoquarternary piperazium complex salt is disclosed in the Patent Application. Specifically, each KMUP compound is dissolved in a mixture of the solution of $C_1$-$C_4$ lower alcohol and water, and the sufficient amount of the mineral acid or organic acid, leading their reaction to obtain the monoquaternary piperazium salt of KMUP compounds. On the other hands, the KMUP-mineral acid or KMUP-organic acid monoquaternary piperazium salt is dissolved in a mixture of the solution of $C_1$-$C_4$ lower alcohol and water, and the sufficient amount of the organic acid or mineral acid, to dissolve the "RX" reactant. Those "RX" moiety of reactant have a carboxyl group of a Statin, the ester derivative of a Statin, a Statin derivative with the protecting group, the alginate sodium, the γ-polyglutamic acid, the sodium polyglutamate, the calcium polyglutamate-alginate sodium, sodium carboxylate methycellulose (sodium CMC) repaglinide and nateglinide, montelukast, cromolyn sodium, nedocromil, gemfibrozil and bezafibrate. The $C_1$-$C_4$ lower alcohol is chosen and the amount of the mixed solution is adjusted upon factors such as the proportion of water, the reacting temperature and the purity of the Statin ester derivative. The resulting quarternary piperazium complex salt of KMUP compounds should be re-dissolved in another mixing solution after filtration, and preferably being re-crystallized under room temperature.

The term "RX" in the present invention may be a mineral acid or an organic acid, selected from the mineral acids including hydrochloric acid (HCl), hydrobromic acid (HBr), hydroiodic acid (HI), sulfuric acid ($H_2SO_4$), nitric acid ($HNO_3$), phosphoric acid ($H_3PO_4$), sodium dihydrogen posphate ($NaH_2PO_4$) and disodium hydrogen phosphate ($Na_2HPO_4$). The organic acids include citric acid, fumaric acid, maleic acid, nicotinic acid, isonicotinic acid, tartaric acid, succinic acid, adipic acid, fatty acid, methanesulfonic acid and phenoxylevulinic acid.

The invention of "PROCESSES FOR PREPARING AMINE SALTS OF SILDENAFIL-ANALOGUES AND USE THEREOF" also represents a complex compound by the formula (I)

formula (III)

wherein R₁ is one selected from a group consisting of a benzene ring having a substituting group being a C1~C5 alkoxy group, a benzene ring having a substituting group being one of a sulfonyl group and an acetyl group, a pyrazolo[4,3d]pyrimidin having a substituting group being one of a C1~C6 alkoxy group and a C1~C6 alkyl group and an imidazo[5,1-f][1,2,4]triazin having a substituting group being one of a C1~C6 alkoxy group and a C1~C6 alkyl group; $R_a$ is one selected from a group consisting of a hydrogen group, a halogen atom, an amino group, a nitro group, a C1~C5 alkyl group and a C1~C5 hydroxyalkyl group; and RX contains a carboxylic group donated from a group consisting of a mineral acid, an organic acid, a Statin derivative, a γ-polyglutamic acid derivative, a Vitamin and a sodium carboxylate methycellulose, wherein $RX^-$ is an anion of the carboxylic group carrying a negative charge. The above-mentioned halogen refers to fluorine, chlorine, bromine and iodine.

In the formula (III), the (N) herein means linked amine or cyclic amino atoms, i.e., linear, C3~C8 cyclic amines and heterocyclic N—H groups. n is an integer from 0 to 5. The $R_1$, $R_a$ and RX substituting group is explained as above.

Invention embodiments also include a compound of formula (I) and (III), wherein the C1~C6 alkyl means an alkyl moiety containing 1, 2, 3, 4, 5 or 6 carbon atoms.

The amine complex salt is referred as formula (I) or formula (III), prepared according to the embodiments in the present invention. It is proved that the "Sildenafil-analogues monoquaternary piperazinium complex salts" is referred as formula (I) and "Udenafil-analogues amine complex salts" is referred as formula (III) which may demonstrate pro-drug and multiple therapeutic functions.

According to the present invention, the Statin-based drug containing a derivative of the carboxyl group can be selected from the commercial products, referred to Atorvastatin, Cerivastatin, Fluvastatin, Lovastatin, Mevastatin, Pravastatin, Rosuvastatin and Simvastatin, which may be an anion of the above-mentioned groups carrying a negative charge.

A preferred pharmaceutical composition of the invention includes a pharmaceutically accepted carrier and an effective amount of complex compound. These amine complex salts is referred as formula (I) or formula (III), prepared from the Sildenafil-analogues or Udenafil-analogues and a Statin derivative, a γ-polyglutamic acid derivative, a Vitamin, a sodium CMC, respectively. Each formulation of formula (I) or formula (III) pharmaceutical composition may be prepared according to the well-known preparation techniques. The Sildenafil-analogues monoquaternary piperazinium complex salts and Udenafil-analogues amine complex salts are adaptable in the clinical usage of human and cause therapeutic effect disclosed in the present invention.

According to another idea, a pharmaceutical combination product of the invention includes a pharmaceutically accepted carrier and an effective amount of each combined drug. The effective amount of combination product is selected from the group of Statin derivative, γ-polyglutamic acid derivative, Vitamin or sodium CMC to react with Sildenafil-analogues, Udenafil-analogues or its salt, according to the well-known preparation techniques. The combination product of Sildenafil-analogues or Udenafil-analogues and Statin derivative; Sildenafil-analogues or Udenafil-analogues and γ-polyglutamic acid derivative; Sildenafil-analogues or Udenafil-analogues and Vitamin; or Sildenafil-analogues or Udenafil-analogues and sodium CMC, are adaptable in the clinical usage of human and cause therapeutic effect disclosed in the present invention.

Sildenafil-analogues have a general skeletal of hetero substituted group and piperazium structure and the respective hetero substituted group is selected from the group of a pyrazolo[4,3d]pyrimidin or an imidazo[5,1-f][1,2,4]triazin.

Figure 1:
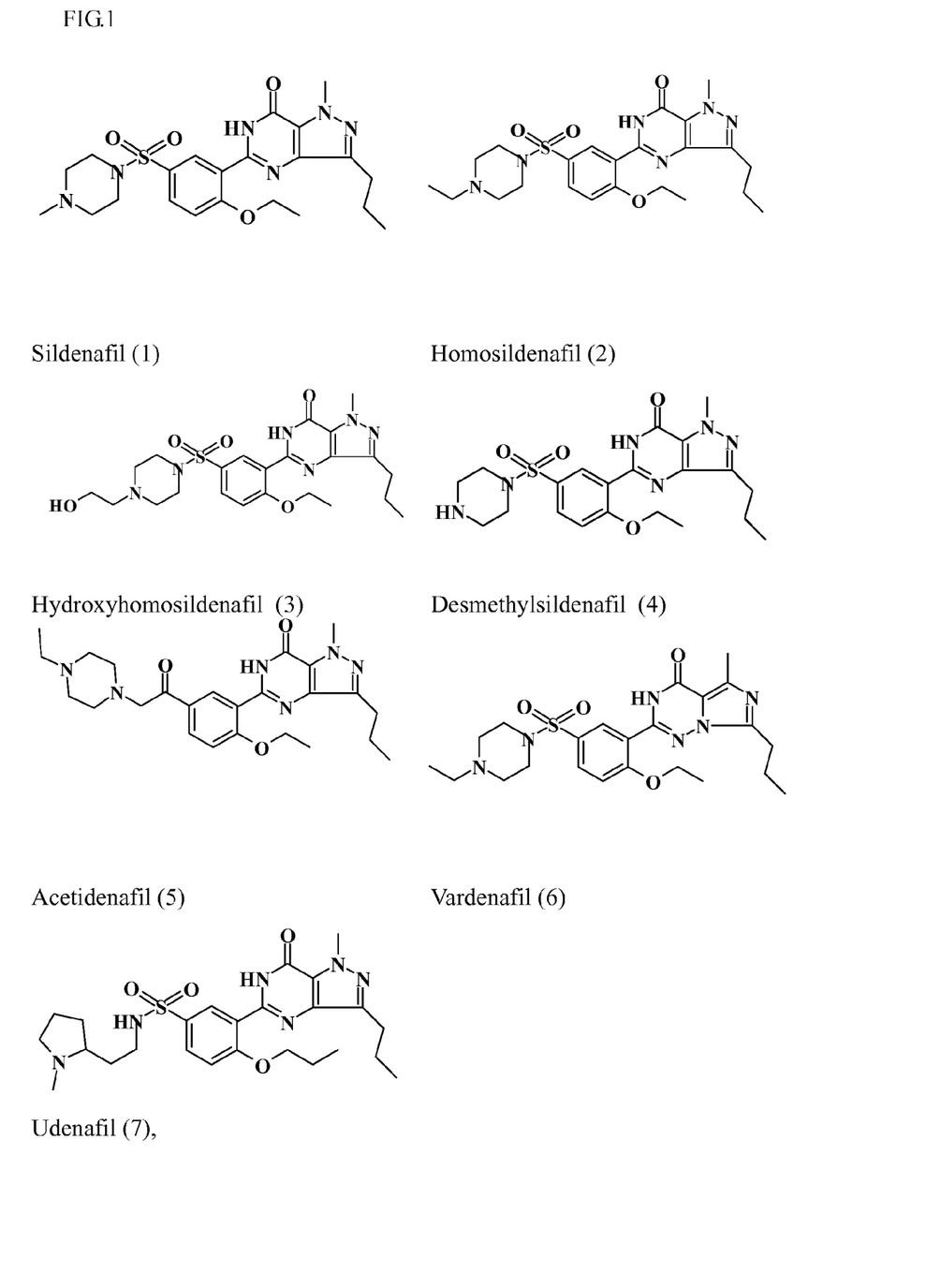
FIG. 1 shows the structures of Sildenafils-analogues.

Sildenafil-analogues monoquaternary piperazinium complex is represented by formula (I), where R1 is selected from the pyrazolo[4,3d]pyrimidin group and sulfonyl group, when Ra is selected from the methyl group, the compound have generic name of Sildenafil whose chemical name is 5-[2-Ethoxy-5-(4-methylpiperazin-1-yl-sulphonyl)phenyl]-1-methyl-3-n-propyl-1,6-dihydro-7H-pyrazolo[4,3 d]pyrimidin-7-one, or 1-[[3-(4,7-Dihydro-1-methyl-7-oxo-3-propyl-1H-pyrazolo[4,3-d]pyrimidin-5-yl)-4-ethoxyphenyl]sulfonyl]-4-methylpiperazine (1). When Ra is selected from the ethyl group, the compound have generic name of Homosildenafil whose chemical name is 5-[2-Ethoxy-5-[(4-ethyl-1-piperazinyl)-sulfonylphenyl]-1,6-dihydro-1-methyl-3-propyl-7H-pyrazolo[4,3-d]pyrimidin-7-one (2). When Ra is selected from the ethanol group (N-hydroxyethyl group), the compound have generic name of Hydroxyhomosildenafil whose chemical name is 1-[[3-(6,7-dihydro-1-methyl-7-oxo-3-propyl-1H-pyrazolo[4,3-d]pyrimidin-5-yl)-4-ethoxyphenyl]-sulfonyl]-4-hydroxyethylpiperazine (3). When Ra is selected from the hydrogen group, the compound have generic name of Desmethylsildenafil whose chemical name is 5-[2-Ethoxy-5-(1-piperazinylsulfonyl)phenyl]-1,6-dihydro-1-methyl-3-propyl-7H-pyrazolo[4,3-d]pyrimidin-7-one (4). Only R1 substituent is selected from an acetyl group changing the sulfonyl group of Homosildenafil, which Sildenafil-analogues have generic name of Acetidenafil whose chemical name is 5-{2-ethoxy-5-[2-(4-ethylpiperazine-1-yl)-acetyl]phenyl}-1-methyl-3-n-propyl-1,6-dihydro-7H-pyrazolo[4,3-d]pyrimidin-7-one (5). When R1 substituent is selected from an imidazo[5,1-f][1,2,4]triazin group in place of the pyrazolo[4,3-d]pyrimidin group of Homosildenafil whose chemical name is 2-[2-Ethoxy-5-(4-ethylpiperazin-1-yl sulfonyl)phenyl]-5-methyl-7-propylimidazo[5,1f][1,2,4]triazin-4(3H)-one (6). Udenafil-analogues amine complex salts is represented by formula (III), where R1 have the pyrazolo[4,3d]pyrimidin group and sulfonyl group, the (N) is pyrollidinyl, and n is an integer 3. When Ra is selected from the methyl group, the compound have generic name of Udenafil whose chemical name is 5-[2-propyloxy-5-(1-methyl-2-pyrollidinylethylamidosulfonyl)phenyl]-1-methyl-3-propyl-1,6-dihydro-7H-pyrazolo[4,3-d]pyrimidine-7-one (7). The compound (6) having generic name of Vardenafil as shown in U.S. Pat. No. 6,362,178 has more divergence skeletal between of the Sildenafil-analogues as described above. These Sildenafil-analogues are described in FIG. 1.

Therefore, the Sildenafil-analogues includes Sildenafil, Homosildenafil, Hydroxyhomosildenafil, Desmethylsildenafil, Acetidenafil, Vardenafil and Udenafil. The Sildenafil may represent those seven compounds, make react with Statin derivative, γ-polyglutamic acid derivative, Vitamin or sodium CMC to form the monoquaternary amine complex salts of Sildenafil-analogues and amine complex salts of Udenafil-analogues. Thereby, Sildenafil-analogues may represent Sildenafil, Homosildenafil, Hydroxyhomosildenafil, Desmethylsildenafil, Acetidenafil, Vardenafil and Udenafil. The involved piperazine or amine moiety, and the statins, γ-polyglutamic acid derivative, Vitamin or sodium CMC may represent the above-mentioned "RX" or "RX⁻" compounds involved in preparing the amine salts in the present invention, if necessary.

Furthermore, the term "RX" substituent can be referred to the Statins or Vitamin, γ-polyglutamic acid sodium, CMC containing a derivative of the carboxyl group and can react with the piperazine group of Sildenafil-analogues, or pyrollidinyl group of Udenafil-analogues, so as to obtain the above amine complex salts according to the method in the present invention. Those synthesized Sildenafil-analogues monoquaternary amine complex salts and Udenafil-analogues amine complex salts may show as pro-drug and multiple therapeutic functions in the body via a chemical or an enzymatic hydrolysis.

Thereby, Sildenafil may represent Sildenafil-analogues and the Statins, γ-polyglutamic acid, Vitamin or sodium CMC may represent the above-mentioned "RX", "RX⁻" substituent, Statins derivative or γ-polyglutamic acid derivative, Vitamin or sodium CMC separately, involved in preparing the Sildenafil-analogues monoquaternary complex salts or Udenafil-analogues amine complex salts in the present invention, if necessary.

According to the present invention, the "RX", "RX⁻" substituent selected from the Statins derivative, γ-polyglutamic acid derivative, Vitamin or sodium CMC which all chemically have a carboxyl moiety, can ionically combine with piperazine moiety of Sildenafil-analogues or pyrollidinyl group of Udenafil-analogues via a chemical pretreatment.

Thus, the lactone ring, ester and protected derivatives of the Statins are available to prepare the above Sildenafil-analogues monoquaternary amine complex salts or Udenafil-analogues amine complex salts in the present invention.

According to the present invention, Statins derivative and γ-polyglutamic acid derivative, Vitamin or sodium CMC separately react with the piperazine group of Sildenafil-analogues or pyrollidinyl group of Udenafil-analogues to prepare the Sildenafil-analogues monoquaternary complex salts or Udenafil-analogues amine complex salts. Preferred Statins derivative are selected from Atorvastatin, Lovastatin, Pitavastatin, Rosuvastatin and Simvastatin, γ-polyglutamic acid derivative are selected from alginate sodium, the γ-polyglutamic acid, the sodium polyglutamate, and the GLT is referred as the co-polymer of Lysine, Glutamate and Tyrosine, and the calcium polyglutamate-alginate sodium, Vitamin is selected from Retinoic Acid, Ascorbic acid, Folic acid, Gamma-Linolenic Acid, nicotinic Acid and Pantothenic acid. Thereby, the Sildenafils-γ-Polyglutamic Acid, Sildenafils-Simvastatinic Acid, Sildenafils-Pramastatinic Acid, Sildenafils-Lovastatinic Acid, Sildenafils-Pitavastatin, Sildenafils-Rosuvastatin Sildenafil-L-Arginine, Sildenafil-CMC, Sildenafil-Mevastatinic acid, Sildenafil-Rosuvastatinic acid, Sildenafils-Lovastatinic Acid, Udenafil-CMC, Udenafil-nicotinic Acid and Udenafil-L-Retinoic Acid are obtained.

The term excipients or "pharmaceutically acceptable carrier or excipients" and "bio-available carriers or excipients" above-mentioned include any appropriate compounds known to be used for preparing the dosage form, such as the solvent, the dispersing agent, the coating, the anti-bacterial or anti-fungal agent and the preserving agent or the delayed absorbent. Usually, such kind of carrier or excipient does not have therapeutic activity itself. Each formulation prepared by combining the derivatives disclosed in the present invention and the pharmaceutically acceptable carriers or excipients will not cause the undesired effect, allergy or other inappropriate effects while being administered to an animal or human. Accordingly, the derivatives disclosed in the present invention in combination with the pharmaceutically acceptable carrier or excipients are adaptable in the clinical usage and in the human. A therapeutic effect can be achieved by using the dosage form in the present invention by the local or sublingual administration via the venous, oral, and inhalation routes or via the nasal, rectal and vaginal routes. About 0.1 mg to 100 mg per day of the active ingredient is administered for the patients of various diseases.

The carrier is varied with each formulation, and the sterile injection composition can be dissolved or suspended in the non-toxic intravenous injection diluents or solvent such as 1,3-butanediol. Among these carriers, the acceptable carrier may be mannitol or water. Besides, the fixing oil or the synthetic glycerol ester or di-glycerol ester is the commonly used solvent. The fatty acid such as the oleic acid, the olive oil or the castor oil and the glycerol ester derivatives thereof, especially the oxy-acetylated type, may serve as the oil for preparing the injection and as the naturally pharmaceutical acceptable oil. Such oil solution or suspension may include the long chain alcohol diluents or the dispersing agent, the carboxylmethyl cellulose or the analogous dispersing agent. Other carriers are common surfactant such as Tween and Spans or other analogous emulsion, or the pharmaceutically acceptable solid, liquid or other bio-available enhancing agent used for developing the formulation that used in the pharmaceutical industry.

The composition for oral administration adopts any oral acceptable formulation, which includes capsule, tablet, pill, emulsion, aqueous suspension, dispersing agent and solvent. The carrier generally used in the oral formulation, taking the tablet as an example, the carrier may be the lactose, the corn starch and the lubricant, and the magnesium stearate is the basic additive. The diluents used in the capsule include the lactose and the dried corn starch. For preparing the aqueous suspension or the emulsion formulation, the active ingredient is suspended or dissolved in an oil interface in combination with the emulsion or the suspending agent, and the appropriate amount of the sweetening agent, for example, the flavors or the pigment is added as needed.

The nasal aerosol or inhalation composition may be prepared according to the well-known preparation techniques. For example, the bioavailability can be increased by dissolving the composition in the phosphate buffer saline and adding the benzyl alcohol or other appropriate preservative, or the absorption enhancing agent. The compound of the present invention may be formulated as suppositories for rectal or virginal administration.

The compound of the present invention can also be administered intravenously, as well as subcutaneously, parentally, muscular, or by the intra-articular, intracranial, intra-articular fluid and intra-spinal injections, the aortic injection, the sterna injection, the intra-lesion injection or other appropriate administrations.

Currently commodity available Statins widely include Atorvastatin, Cerivastatin, Fluvastatin, Lovastatin, Mevastatin, Pravastatin, Rosuvastatin and Simvastatin. The chemical names of various Statins are listed in Table 1. Lovastatin (disclosed in U.S. Pat. No. 4,231,938) and Simvastatin (disclosed in U.S. Pat. No. 4,444,784) are administered in a lactone form. After being absorbed, the lactone ring is opened in the liver by a chemical or an enzymatic hydrolysis, and the active hydroxy acid (Statinic acid) is generated. Pravastatin (disclosed in U.S. Pat. No. 4,346,227) is administered as the sodium salt. Fluvastatin (disclosed in U.S. Pat. No. 4,739,073) and Cerivastatin (disclosed in U.S. Pat. Nos. 5,006,530 and 5,177,080), also administered as the sodium salts, are entirely synthetic compounds that are structurally distinct from a kind of drug to which the fungal derivatives including a hexahydronaphthalene ring belong. Both Rosuvastatin and Pitavastatin are novel lipid-lowering drugs, called "superstatins". Atorvastatin is disclosed in U.S. Pat. No. 4,681,893, and the character that the free acid of Atorvastatin is prone to lactonization has been disclosed in U.S. Pat. No. 5,273,995.

TABLE 1

Chemical names of the Statins

| Commercial products | Chemical names |
|---|---|
| Atorvastatin intermediate L-1 | tert-Butyl(4R,6R)-2-[[[6-(2-4-fluorophenyl)-5-isopropyl-3-phenyl-4-(phenylcarbamoyl) pyrrol-1-yl]ethyl]-2,2-dimethyl-1,3-dioxan-4-yl]acetate(4R, 6R)-6-[2-[2-(4-fluorophenyl)-5-(1-methylethyl)-3-phenyl-4-[(phenylamino)carbonyl]-1H-pyrrol-1-yl]ethyl]-2,2-dimethyl-1,3-Dioxane-4-acetic acid 1,1-dimethylethyl ester |
| Atorvastatin Calcium salt | [R—(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt |
| Atorvastatin lactone | 2R-trans)-5-(4-fluorophenyl)-2-(1-methylethyl)-N,4-diphenyl-1-[2-tetrahydro-4-hydroxy-6-oxo-2H-pyran-2-yl)ethyl]-1H-pyrrole-3-carboxamide |
| Cerivastatin sodium salt | sodium (E,3R,5S)-7-[4-(4-fluorophenyl)-5-(methoxymethyl)-2,6-di(propan-2-yl)pyridin-3-yl]-3,5-dihydroxyhept-6-enoate |
| Fluvastatin sodium salt | Sodium (E,3S,5R)-7-[3-(4-fluorophenyl)-1-propan-2-ylindol-2-yl]-3,5-dihydroxyhept-6-enoate |
| Lovastatin sodium salt | 1S-[1a(bS,dS),2a,6b,8b(R),8aa]]-1,2,6,7,8, 8a-Hexahydro-b,d-dihydroxy-2,6-dimethyl-8-(2-methyl-1-oxobutoxy)-1-naphthaleneheptanoic acid monosodium salt |
| Mevastatin ester | 2-Methyl-butanoic acid [1S-[1-α(R*),7-β,8-β(2S*,4S*),α-β]]-1,2,3,7,8,8a-hexahydro-7-methyl-8-[2-(tetrahydro-4-hydroxy-6-oxo-2H-pyran-2-yl)ethyl]-1-naphthalenyl ester |
| Pitavastatin calcium salt | (3R,5S,6E)-7-[2-cyclopropyl-4-(4-fluorophenyl)-3-quinolyl]-3,5-dihydroxy-6-heptenoate |
| Pravastatin sodium salt | [1S-[1a(bS,dS),2a,6b,8b(R),8aa]]-1,2,6,7,8, 8a-Hexahydro-b,d,6-trihydroxy-2-methyl-8-(2-methyl-1-oxobutoxy)-1-naphthalene-heptanoic acid monosodium salt |
| Rosuvastatin Calcium salt | bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium |
| Simvastatin Sodium salt | Ammonium (3R,5R)-7-[(1S,2S,6R,8S,8aR)-8-(2,2-dimethylbutyryloxy)-1,2,6,7,8,8a-hexahydro-2,6-dimethyl-1-naphthyl]-3,5-dihydroxyheptanoate |

According to the above-mentioned, the piperazium group or pyrollidinyl group of Sildenafil-analogues reacts with the carboxylic acid moiety of "RX" in the present invention. For example, Atorvastatin calcium salt can be reacted with Sildenafil HCl, to perform the double decomposition exchange reaction and to release sodium chloride, potassium chloride, calcium chloride or ammonium chloride in a solvent system of water and ethyl alcohol mixture. Such Statin calcium salt or sodium salt contacts with the Sildenafil HCl to form a water soluble sodium chloride or calcium chloride. The non-salt type free acid Statin will react with the piperazium group or pyrollidinyl group of Sildenafil and form the "Sildenafil-Statins complex salt" or more favorable "Sildenafil-analogues-Statinic acid complex salt".

U.S. Pat. No. 5,298,627 discloses that (4R-cis)-1-[2-[6-[2-(diphenylamino)-2-oxoethyl]-2,2-dimethyl-1,3-dioxan-4-yl]ethyl]-5-(4-fluorophenyl)-2-(1-methylethyl)-N,4-diphenyl-1H-pyrrole-3-carboxamide is dissolved in methanol and reacted with hydrochloric acid to form [R—(R*,R*)]-5-(4-fluorophenyl)-β,δ-dihydroxy-2-(1-methylethyl)-N,N,4-triphenyl-3-[(phenylamino)carbonyl]-1H-pyrrole-1-heptanamide, which is mixed with methanol and sodium hydroxide. The filtrate is washed with tert-butyl methyl ester and the aqueous layer is acidified by using hydrochloric acid, then extracted with tert-butyl methyl ester to afford the sodium salt of [R—(R*,R*)]-2-(4-fluorophenyl)-β,δ-dihydroxy-5-(1-methylethyl)-3-phenyl-4-[(phenylamino)carbonyl]-1H-pyrrole-1-heptanoic acid.

U.S. Pat. No. 5,489,690 has described another preparation method on step 6. Modifying the procedure analogous to step 6 by adding equimolar amount of Sildenafils hydrochloride can prepared the Sildenafils-Statinic monoquarternary amine complex salts.

An analogous acetamide structure in Atorvastatin can be converted into a Sildenafils-analogues monoquarternary amine complex salt. For example, (4R-cis)-6-(2-aminoethyl)-2,2-dimethyl-N,N-bis(phenylmethyl)-1,3-dioxane-4-acetamide is firstly converted to [R—(R*,R*)]-5-(4-fluorophenyl)-β,δ-dihydroxy-2-(1-methylethyl)-4-phenyl-3-[(phenylamino)carbonyl]-N,N-bis(phenylmethyl)-1H-pyrrole-1-heptanamide which is reacted and further converted to the Statinic acid complex salt with Sildenafils-analogues monoquarternary amine group. Moreover, (4R-cis)-6-(2-aminoethyl)-N,N-diethyl-2,2-dimethyl-1,3-dioxane-4-acetamide is converted to [R—(R*,R*)]-N,N-diethyl-5-(4-fluorophenyl)-β,δ-dihydroxy-2-(1-methylethyl)-4-phenyl-3-[(phenylamino)carbonyl]-1H-pyrrole-1-heptanamide which is further converted to a complex salt of the Sildenafils-analogues-Statinic acid. In an analogous manner is carried out using the conditions above-described, (4R-cis)-6-(2-aminoethyl)-N-butyl-N,2,2-trimethyl-1,3-dioxane-4-acetamide is converted to [R—(R*,R*)]-N-butyl-5-(4-fluorophenyl)-β,δ-dihydroxy-N-methyl-2-(1-methylethyl)-4-phenyl-3-[(phenylamino)carbonyl]-1H-pyrrole-1-heptanamide then reacted to form a complex salt of the Sildenafils-Statinic acid. The (4R-cis)-6-(2-amino ethyl)-N-(1,1-dimethylethyl)-2,2-dimethyl-N-(phenylmethyl)-1,3-dioxane-4-acetamide is converted to [R—(R*,R*)]-N-(1,1-(dimethylethyl))-5-(4-fluorophenyl)-β,δ-dihydroxy-2-(1-methylethyl)-4-phenyl-3-[(phenylamino)carbonyl]-N-(phenylmethyl)-1H-pyrrole-1-heptanamide which is further reacted to form a complex salt of the Sildenafils-Statinic acid. Furthermore, the (4R-cis)-1-[[6-(2-aminoethyl)-2,2-dimethyl-1,3-dioxan-4-yl]-acetyl]piperidine also can converted to [R—(R*,R*)]-1-[3,5-dihydroxy-7-oxo-7-(1-piperidinyl) heptyl]-5-(4-fluorophenyl-2-(1-methylethyl)-N-4-diphenyl-1H-pyrrole-3-carboxamide then forms a complex salt of the Sildenafils-analogues-Statinic acid with the Sildenafils-analogues monoquarternary piperazium group.

The structure of commercial Statin calcium salt includes two molecules of Statins and one molecule of calcium. The so-called hemicalcium salt is referred to a combination of one molecule of Statins and one molecule of calcium. Rosuvastatin, its calcium salt and its lactone form are disclosed in U.S. Pat. No. 5,260,440, which obtains the methyl ester of Rosuvastatin under reflux followed by reduction with $NaBH_4$. Further, the ester is then hydrolyzed with sodium hydroxide in ethanol solution at room temperature, followed by removal of the ethanol and addition of ether, to obtain the sodium salt of Rosuvastatin. Additionally, the Rosuvastatin composition disclosed in U.S. Pat. No. 6,316,460 includes a multivalent phosphate salt of Rosuvastatin. According to the process of the present invention, dissolved Rosuvastatin sodium salt in water under a nitrogen atmosphere, and added into the Sildenafils, followed by the precipitation and crystallization, the Sildenafils-Rosuvastatinic acid monoquarternary piperazium complex salt is formed.

Statins can be prepared through an intermediate in which one or both of the hydroxyls in the diol pentanoic acid group (open-ring form) or the hydroxyl of the lactone group (ring-close form) is protected via a hydrolyzable protecting group and the carboxyl group is protected via an ester derivative. U.S. Pat. No. 5,260,440 discloses the preparation of Rosuvastatin. U.S. Pat. Nos. 6,002,021 and 4,444,784 disclose a process for preparing Simvastatin, which uses the cyclic protecting group such as the dioxane, the cyclic sulfate, the cyclic phosphate and the borylidene to substitute the alkyl or aryl timely. Additionally, WO 95/13283 discloses the boric acid as the protecting group, the U.S. Pat. No. 5,159,104 discloses an esterification proceeded by the acetic anhybride and U.S. Pat. No. 6,100,407 also discloses some protecting groups.

Piperazium group or pyrollidinyl group of Sildenafils-analogues reacts with the carboxylic acid moiety of Statins in the present invention. The Atorvastatin can be converted into Atorvastatin semicalcium salt although it is protected by the ester group. The process for preparing Sildenafils-analogues statin monoquarternary amine group complex salt described in the present invention is also applicable in preparing the ester derivative and the protected derivative of Statin. In the process, the metallic hydroxide such as sodium, potassium and calcium and the ammonia hydroxide are added to mildly heat the reaction of a mixture solution of the ester derivative of the statin, Sildenafils-analogues, water and $C_1$ to $C_4$ alcohol for preventing the decomposition of the Statin and the prodrug thereof.

Preferred Statins are Atorvastatin, Lovastatin, Pitavastatin, Rosuvastatin and Simvastatin, and the Statin structure of those drugs are hydrolized by metallic hydroxide, such as sodium, potassium, calcium, and ammonia hydroxide, and acids useful to hydrolyze the ester group of Statin.

The formation of Sildenafils-Statinic acid complex from Sildenafils HCl salt is easily obtained by reacting Sildenafils HCl with the equal molar sodium hydroxide in the presence of hydrolyzable Statins or Statins ester and derivatives. The sodium ion precedes the equal molar neutralization can take place within the HCl part of Sildenafils HCl, and the resulted NaCl is dissolved in the hydrated alcohol solution. The Statin shows the ionic state, the free state or being mixed with other unreacted ester derivative of the statin in a mixing solution of water and $C_1$-$C_4$ lower alcohol (i.e. the ethanol and the isopropanol). By following the amount of each Statin derivative hydrolyzed by the sufficient amount of sodium hydroxide, the term "sufficient amount of piperazium group or pyrollidinyl group" is about the amount of equal mole.

On the other hands, calcium hydroxide also fulfills the dual role, which functions as the alkaline catalyst for hydrolyzing the ester, supplies the calcium ions for forming the semicalcium salt, and proceeds the equal molar neutralization with the HCl of the Sildenafils-analogues HCl salt respectively, to generate one or two molecular of the precipitation of the Sildenafils-analogues-Statinic acid complex salt. The residual Statin derivative compound that does not react completely with Sildenafils is dissolved in the hydrated alcohol solution. In the process of the present invention, the state of the reaction is monitored by Thin Layer Chromatography (TLC) and the developing solvent is MeOH:Ethyl acetate=1:9.

The excess amount of Sildenafils HCl salt is required to react with the alginate sodium, the γ-polyglutamic acid, the sodium polyglutamate and the calcium polyglutamate-alginate sodium and sodium CMC so as to complete the reaction and to synthesize the sodium-removable products. The residual Sildenafils HCl salt is dissolved in the filtrate in the hydrated alcohol solution after the precipitation is filtered.

The synthesis of monoquarternary amine complex salt is performed by mixing the solution of $C_1$-$C_4$ lower alcohol and water, and the amount of the mixed solution is sufficient to dissolve the reactant. The "RX" moiety of reactant has a carboxyl group of a Statin, the ester derivative of a Statin, a Statin derivative with the protecting group, the alginate sodium, the γ-polyglutamic acid, the sodium polyglutamate, the calcium polyglutamate-alginate sodium and sodium CMC. The $C_1$-$C_1$ lower alcohol is chosen and the amount of the mixed solution is adjusted upon factors such as the proportion of water, the reacting temperature and the purity of the Statin ester derivative. The $C_1$-$C_4$ lower alcohol usual selected the ethanol or isopropyl alcohol (IPA), and preferred mixture solvent reducing the concentrations of alcohol, eg. containing about 5% to 30% water in ethanol or IPA, more preferably about 10% water in 90% ethanol (v/v) or IPA. The Statin ester derivative is hydrolyzed in the alkaline catalyst, and which is added in the mixed solution in an amount about 10 mmoles $L^{-1}$ to about 1 mole $L^{-1}$. The temperature of the mixing solution should be heated to about 40° C. to 70° C. in a sequence to reflux the mixed solution for accelerating the reaction. The resulting Sildenafils monoquarternary amine complex salts should be re-dissolved in another mixing solution after filtration, and preferably being re-crystallized under room temperature.

Other objects, advantages and efficacies of the present invention will be described in detail below taken from the preferred embodiments with reference to the accompanying drawings, in which:

DETAILED DESCRIPTION OF THE PREFERRED EMBODIMENT

Figure 2:
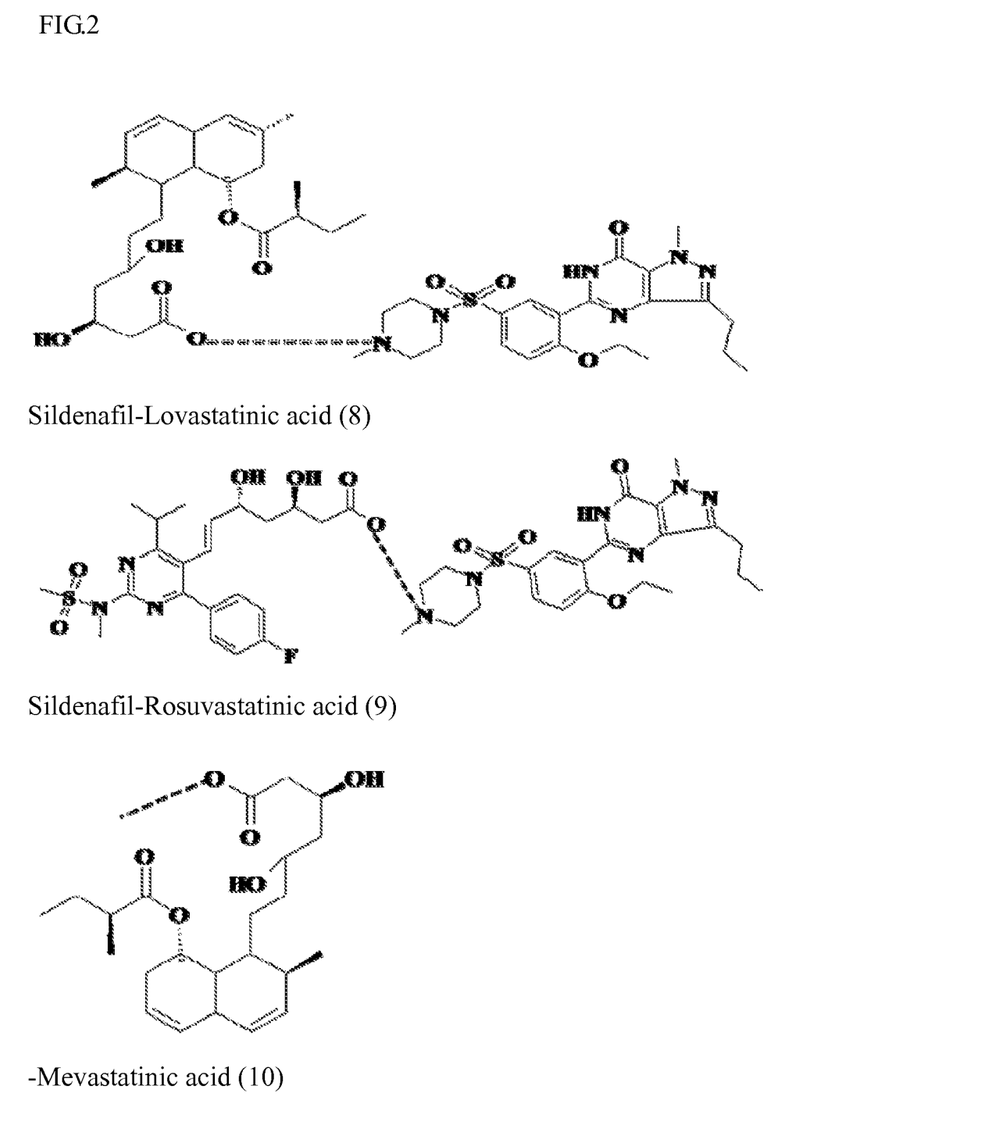
FIG. 2 shows the structures of the Sildenafils-Statin monoquarternary amine salts.

The Sildenafil-analogues monoquarternary amine complex salts prepared according to the embodiments in the present invention are shown as FIG. 2. The complex salts show lipid-lowering effect (Table 2), the effect of rats with monocrotaline (MCT)-induced pulmonary hypertension (Tables 3), and effect on inhibiting pulmonary fibrosis (Table 4) in the following activity assay. Such assays illustrate that the Sildenafil-analogues monoquarternary amine complex salts of the formula (I) or Udenafil-analogues amine complex salts of the formula (III) and their pharmaceutically compositions show useful pharmacological properties in animal experiments. In particular, they effect a marked reduction in the blood level values of cholesterol and triglycerides and, on the basis of these lipid-lowering properties, pulmonary hypertension, and on inhibiting pulmonary fibrosis, can be used in human medicine for those diseases. Such diseases are primarily cardiovascular disorders, inter alia thrombosis, arteriosclerosis, myocardial infarction and angina pectoris. The Sildenafil-analogues monoquarternary amine complex salts or Udenafil-analogues amine complex salts mentioned can be administered to these animals enterally or parenterally, and in view of human administration in particular also orally.

Therefore, the present invention is truly a rare novel invention and industrial applicable. Additionally, any modification may be practiced without leaving the scope of the appended claims by one of skill in the art.

The present application "PROCESSES FOR PREPARING AMINE SALTS OF SILDENAFIL-ANALOGUES AND USE THEREOF" will be fully understood from the following embodiments, and thereby being accomplished based thereon by one skilled in the art. However, the practice of the present application is not intended to limit to the following embodiments in its practice, and the skilled person can still conduct other embodiments according to the spirit of embodiments presented herein that belong to the scope of this invention.

Experimental Materials and Methods:

Activity Assay:

1. The Lipid-Lowering Effect in C57BL/6J Mice 8-week C57BL/6J mice are divided into standard diet (STD) group and the high-fat diet (HFD) group. In the HFD group, the Simvastatin (5 mg/kg), Sildenafil-Atorvastatinic acid complex salt, Sildenafil-Rosuvastatinic acid complex salt, Sildenafil-Simvastatinic acid complex salt (2.5 mg/kg) are separately administered orally. After 21 days, the amounts (mg/d1) of the triglyceride (TG), the total cholesterol (Tot.-C), the high density lipoprotein cholesterol (HDL-C), and the low density lipoprotein cholesterol (LDL-C) of six mice for each group are measured as shown in Tables 2.

TABLE 2

The lipid-lowering effect in C57BL/6J mice

|  | TG | Tot.-C | HDL-C | LDL-C |
|---|---|---|---|---|
| STD | 107.2 ± 6.1 | 78.67 ± 1.9 | 60.44 ± 1.6 | 6 ± 0.3 |
| HFD | 166.8 ± 5.3 | 166.8 ± 13.4 | 68.4 ± 3.5 | 31.33 ± 7 |
| Simvastatin (5 mg/kg) | 82.67 ± 6.3 | 133.67 ± 4.3 | 103.18 ± 2.5 | 15.3 ± 1.3 |
| Sildenafil-Simvastatinic acid complex salt (2.5 mg/kg) | 81.2 ± 4.4 | 129.7 ± 1.4 | 102.4 ± 2.3 | 17.3 ± 1.4 |
| Sildenafil-Rosuvastatinic acid complex salt (2.5 mg/kg) | 83.2 ± 5.3 | 131.7 ± 1.6 | 103.4 ± 1.5 | 15.2 ± 1.7 |
| Sildenafil-Atorvastatinic acid complex salt (2.5 mg/kg) | 79.2 ± 4.6 | 130.7 ± 1.7 | 97.6 ± 2.8 | 16.8 ± 1.8 |

2. The Monocrotaline (MCT)-Treated Rats Show the Decreased Pulmonary Aterial Hypertension Pulmonary aterial hypertension in MCT-treated rats is caused on day 21 after the intracutaneously injection. Orally separately administered Sildenafil-Simvastatinic acid complex salt and Sildenafil-γ-polyglutamic acid complex salt (2.5 mg/kg), every day may inhibit the male Wistar rats treated with MCT, which show the effect of decreasing the pulmonary artery blood pressure (PABP).

TABLE 3

Inhibition of the pulmonary artery blood pressure

| Group | Does (mg/kg/day) | PABP (mmHg) |
|---|---|---|
| Control group |  | 11 ± 1.4 |
| MCT (60 mg, intracutaneously) |  | 25 ± 2.3 |
| Sildenafil-Simvastatinic acid complex salt | 2.5 mg, p.o. | 12 ± 1.5 |
| Sildenafil-γ-polyglutamic acid complex salt | 2.5 mg, p.o. | 11 ± 0.8 |

3. Sildenafil-Simvastatinic Acid Complex Salts Inhibit the Lung Fibrosis in Mice Induced by Bleomycin (BM) Mediated Via TGF-β Expression in Lung The increased amount of the synthetic collagen and the generation of the macrophage in alveolus may facilitate the formulation of transforming growth factor beta (TGF-β), and the expression of TGF-β is looked as a biomarker of the lung fibrosis. The simvastatin (5 mg/kg) and Sildenafil-Simvastatinic acid complex salts (2.5 mg/kg) are orally administered to the mice for inhibiting the lung fibrosis induced by TGF-β expression in tracheal irrigation solution that resulted from 60 mg/kg BM inhalation (Table 4). The state of the TGF-β expression in the irrigation solution is measured by the enzyme immunoassay (EIA).

TABLE 4

The inhibition of lung fibrosis signaling TGF-β

| Drug (mg/kg) | Changed amount of the lung TGF-β |
|---|---|
| Bleomycin (BM, 60) |  |
| BM + Simvastatin (5) | 40 ± 4.3%* |
| BM + Sildenafil-Simvastatinic acid (2.5) | 43 ± 1.8%* |

*$P < 0.05$, which represents the significant difference in comparison with the control group.

EXAMPLES

The respective amount (g) of the compounds provided in the following examples is given by the equal molecular weight of each compound (2 Mol or 2 mMol). Obtained part of these compounds is used in activity assays in this invention.

Statinic acid indicates the open-lactone type Statin having the carboxylic acid moiety. For example, Simvastatinic acid indicates that Simvastatin chemically with the carboxylic acid moiety. Atorvastatinic acid, Rosuvastatinic acid, Lovastatinic acid and other Statinic acid indicate that Atorvastatin, Rrosuvastatin and Lovastatin chemically with the carboxylic acid moiety.

Example 1

Preparation of Sildenafil-Lovastatinic Acid Complex Salt (8)

Lovastatin (8.8 g) is dissolved in ethanol (50 mL), under room temperature the aqueous solution of sodium hydroxide (4 g/60 ml) is added to result an ethanol solution of Lovastatinic acid sodium (300 mL) for use.

In a flask equipped with a magnetic stirrer, Sildenafil citrate (13.2 g) is dissolved in a mixture of ethanol (100 mL) and water (30 mL), an ethanol solution of Lovastatinic acid sodium is added then reacted at 50° C. for 20 mins. After cooling, a white precipitate is obtained and the sodium citrate is removed by filtration. The methanol (100 mL) is added under room temperature and being incubated over night for re-precipitation. The Sildenafil-Lovastatinic acid complex salt (16.8 g) is obtained after filtering the crystal.

Example 2

Preparation of Sildenafil-Rosuvastatinic Acid Complex Salt (9)

Rosuvastatin (10.5 g) dissolved in ethanol (50 mL), under room temperature the aqueous solution of sodium hydroxide (4 g/60 ml) is added to result an ethanol solution of Rosuvastatinic acid sodium (300 mL) for use.
In a flask equipped with a magnetic stirrer, Sildenafil citrate (9.5 g) is dissolved in a mixture of ethanol (100 mL) and water (30 mL), added an ethanol solution of Rosuvastatinic acid sodium then reacted at 50° C. for 20 mins. After cooling, a white precipitate is obtained and the sodium citrate is removed by filtration. The methanol (100 mL) is added under room temperature and being incubated over night for re-precipitation. The Sildenafil-Rosuvastatinic acid complex salt (16.5 g) is obtained after filtering the crystal.

Example 3

Preparation of Sildenafil-Mevastatinic Acid Complex Salt (10)

Sildenafil citrate (9.5 g) is dissolved in a mixture of ethanol (10 mL) and HCl (1N, 60 mL) for use.
In a flask equipped with a magnetic stirrer, Mevastatin (4 g) dissolved in ethanol (50 ml) is poured, to which an aqueous solution of sodium hydroxide (4 g/60 ml) is added under room temperature. After 10 mins, the above-mentioned Sildenafil citrate in the ethanol solution is added for reacting at 50° C. for 20 mins, and the mixture is rapidly filtrated and stood one hour for re-crystallization to give the Sildenafil-Mevastatinic acid complex salt 12.8 g.

Example 4

Preparation of Sildenafil-Atorvastatinic Acid Complex Salt

In a flask equipped with a magnetic stirrer, Atorvastatinic acid (11.2 g) dissolved in ethanol (50 ml) is poured, to which an aqueous solution of sodium hydroxide (4 g/60 ml) is added under room temperature. After 10 mins, the above-mentioned Sildenafil citrate in the ethanol solution is added for reacting at 50° C. for 20 mins, and the mixture is rapidly filtrated and stood one hour for crystallization to give the Sildenafil-Atorvastatinic acid complex salt 16.8 g.
In a flask equipped with a magnetic stirrer, Atorvastatinic acid calcium (11.6 g) dissolved in an aqueous solution of HCl (1N, 60 mL) is poured, to which a sodium hydroxide solution (6 g/60 ml) is added under room temperature. After 10 mins, the above-mentioned Sildenafil citrate in the ethanol solution is added for reacting at 50° C. for 20 mins, and the mixture is rapidly filtrated to remove sodium citrate and stood for one hour for re-crystallization to give the Sildenafil-Atorvastatinic acid complex salt 16.4 g.

Example 5

Preparation of Sildenafil-γ-Polyglutamate Complex 20 g of sodium γ-polyglutamate is dissolved in water to form a 5% viscous aqueous solution (40 ml). Sildenafil citrate (19 g) is added to the solution and the mixture is stirred at 50° C. for 1 hr to obtain a white precipitate. The solution is poured out then the ethanol (100 ml) is added for dehydration. Ethanol (100 ml) is added additionally to wash out the unreacted Sildenafil, over night and warmed at 50° C. in water bath and cooled at room temperature over night to obtain the precipitate of Sildenafil-γ-Polyglutamate complex complex (26.4 g).

Example 6

Preparation of Sildenafil-CMC Complex 20 g of sodium CMC is dissolved in water to form a 5% viscous aqueous solution (40 ml). Sildenafil citrate (13.3 g) is added to the solution and the mixture is stirred at 50° C. for 1 hr to obtain a white precipitate. The solution is poured out then the ethanol (100 ml) is added for dehydration. Ethanol (100 ml) is added additionally to wash out the unreacted Sildenafil, over night and warmed in water bath at 50° C. and cooled at room temperature over night to obtain the precipitate of Sildenafil-CMC complex (29.6 g).

Example 7

Preparation of Sildenafil-L-Arginine Complex

Sildenafil citrate (9.5 g) is dissolved in a mixture of ethanol (10 mL) and HCl (1N, 60 mL), then reacted at 50° C. for 10 mins. Under room temperature, the methanol is added for incubating over night and crystallization. Then, the crystal is filtrated to obtain precipitate of Sildenafil HCl (6.4 g) for use.
Arginine (3.5 g) is dissolved in ethanol (10 mL) and an aqueous solution of sodium hydroxide (4 g/60 ml) is added under room temperature, to form an ethanol solution of Arginine sodium for use.
In a flask equipped with a magnetic stirrer, Sildenafil HCl (8.8 g) is dissolved in a mixture of ethanol (100 mL) and water (30 mL), added an ethanol solution of Arginine sodium then reacted at 50° C. for 60 mins. After cooling, a white precipitate is obtained and the sodium chloride is removed by filtration. The methanol is added under room temperature and being incubated over night for re-precipitation. The Sildenafil-L-Arginine complex salt (10.8 g) is obtained after filtering the crystal.

Example 8

Preparation of Sildenafil-L-Retinoic Acid Complex

Retinoic Acid (6.0 g) is dissolved in ethanol (10 mL) and an aqueous solution of sodium hydroxide (4 g/60 ml) is added under room temperature, to form an ethanol solution of Retinoic acid sodium for use.
In a flask equipped with a magnetic stirrer, Sildenafil HCl (8.8 g) is dissolved in a mixture of ethanol (100 mL) and water (30 mL), added an ethanol solution of Retinoic acid sodium then reacted at 50° C. for 60 mins. After cooling, a white precipitate is obtained and the NaCl is removed by filtration. The methanol (100 mL) is added under room temperature and being incubated over night for re-precipitation. The Sildenafil-Retinoic acid complex salt (12.8 g) is obtained after filtering the crystal.

Example 9

Preparation of Udenafil-CMC Complex

Udenafil HCl (10.3 g) is dissolved in a mixture of ethanol (10 mL) and HCl (1N, 60 mL), then reacted at 50° C. for 10 mins. Under room temperature, the methanol is added for incubating over night and crystallization. Then, the crystal is filtrated to obtain precipitate of Udenafil HCl (8.8 g) for use.

20 g of sodium CMC is dissolved in water to form a 5% viscous aqueous solution (40 ml). Udenafil HCl (20.6 g) is added to the solution and the mixture is stirred at 50° C. for 1 hr to obtain a white precipitate. The solution is poured out then the ethanol (100 ml) is added for dehydration. Ethanol (100 ml) is added additionally to wash out the unreacted Udenafil, over night and warmed in water bath at 50° C. and cooled at room temperature over night to obtain the precipitate of Udenail-CMC complex (32.8 g).

Example 10

Preparation of Udenafil-Nicotinic Acid Salt

Udenafil (10.3 g) is dissolved in a mixture of ethanol (10 mL) and nicotinic acid (2.4 g) and reacted at 50° C. for 20 min, the methanol is added thereinto under room temperature and the solution is incubated over night for crystallization and filtrated to obtain Udenafil-Nicotinic acid salt (11.6 g).

Example 11

Preparation of Udenafil-L-Retinoic Acid Complex

Retinoic Acid (6.0 g) is dissolved in ethanol (10 mL) and an aqueous solution of sodium hydroxide (4 g/60 ml) is added under room temperature, to form an ethanol solution of Retinoic acid sodium for use.

In a flask equipped with a magnetic stirrer, Udenafil HCl (11 g) is dissolved in a mixture of ethanol (100 mL) and water (30 mL), added an ethanol solution of Retinoic acid sodium then reacted at 50° C. for 60 mins. After cooling, a white precipitate is obtained and the NaCl is removed by filtration. The methanol (100 mL) is added under room temperature and being incubated over night for re-precipitation. The Udenafil-Retinoic acid complex salt (15.8 g) is obtained after filtering the crystal.

Example 12

The Tablet Formulae of Sildenafil-CMC Complex

Tablets are prepared using standard mixing and formation techniques as described in U.S. Pat. No. 5,358,941, to Bechard et al., issued Oct. 25, 1994, which is incorporated by reference herein in its entirety.

| Sildenafil-CMC complex | 0.1 g |
|---|---|
| Lactose | qs |
| Corn starch | qs |

Example 13

The Formulae of Sildenafil-Atorvastatin Complex for Treating Pulmonary Hypertension of Children (BID)

| Sildenafil-Atorvastatin Complex | 0.05 g |
|---|---|
| Lactose | qs |
| Corn starch | qs |

Example 14

The Formulae of Sildenafil-Simvastatin Complex for Treating Pulmonary Hypertension of Children

| Sildenafil-Simvastatin Complex | 0.05 g |
|---|---|
| Lactose | qs |
| Corn starch | qs |

Example 15

The Capsule Formulae of Sildenafil-Lovastatin Complex for Treating Pulmonary Hypertension of Children

| Sildenafil-Atorvastatin Complex | 0.05 g |
|---|---|
| Lactose | qs |
| Corn starch | qs |

Example 16

The Capsule Formulae of Sildenafil-Atorvastatin Complex for Treating Male Sex Organ Erection (One Dose)

| Sildenafil-Atorvastatin Complex | 0.2 g |
|---|---|
| Lactose | qs |
| Corn starch | qs |

Example 17

The Formulae of Sildenafil-L-Arginine Complex in Lotion Preparation or Ointment for Treating Male Alopecia

| Sildenafil-L-Arginine complex | 10% |
|---|---|
| Alcohol | qs |
| Propylene glycol | qs |
| /or Lanolin | qs |

Example 18

The formulae of Sildenafil-Retinoic Acid Complex in Lotion Preparation or Ointment for Treating Male Alopecia

| Sildenafil-Retinoic acid complex | 10% |
|---|---|
| Alcohol | qs |
| Propylene glycol | qs |
| /or Lanolin | qs |

More various embodiments are disclosed as follows.
1. A complex salt includes a structure of formula (I)

wherein $R_1$ is one selected from a group consisting of a benzene ring having a substituting group being a C1~C5 alkoxy group, a benzene ring having a substituting group being one of a sulfonyl group and an acetyl group, a pyrazolo[4,3d]pyrimidin having a substituting group being one of a C1~C6 alkoxy group and a C1~C6 alkyl group and an imidazo[5,1-f][1,2,4]triazin having a substituting group being one of a C1~C6 alkoxy group and a C1~C6 alkyl group;

$R_a$ is one selected from a group consisting of a hydrogen group, a halogen atom, an amino group, a nitro group, a C1~C5 alkyl group and a C1~C5 hydroxyalkyl group; and RX contains a carboxylic group donated from a group consisting of a mineral acid, an organic acid, a Statin derivative, a Vitamin, a γ-polyglutamic acid derivative and a sodium CMC, wherein $RX^-$ is an anion of the carboxylic group carrying a negative charge.

2. According to example 1, wherein RX is a Statin derivative being one selected from a group consisting of Atorvastatin, Cerivastatin, Fluvastatin, Lovastatin, Mevastatin, Pravastatin, Rosuvastatin and Simvastatin.

3. According to example 1, wherein RX is the γ-polyglutamic acid derivative being one selected from a group consisting of an alginate sodium, a γ-polyglutamic acid, a sodium polyglutamate, a GLT and a calcium polyglutamate-alginate sodium.

4. According to example 1, wherein RX is the Vitamin being one selected from a group consisting of Retinoic Acid, Ascorbic acid, Folic acid, Gamma-Linolenic Acid, Nicotinic Acid and Pantothenic acid.

5. According to example 1, R1 is one selected from a group consisting of a benzene ring having a substituting group being a C1~C5 alkoxy group, a benzene ring having a substituting group being one of a sulfonyl group and a pyrazolo[4,3d]pyrimidin having a substituting group being a C1~C6 alkyl group;

Ra is one selected from a group consisting of a hydrogen group, a C1~C5 alkyl group and a C1~C5 hydroxyalkyl group;

RX substituent contains a carboxylic group donated from one of a Statin derivative, a Vitamin, a γ-polyglutamic acid derivative and a sodium CMC; and $RX^-$ substituent is an anion of the carboxylic group carrying a negative charge.

6. According to example 1, R1 is one selected from a group consisting of a benzene ring having a substituting group being a C1~C5 alkoxy group, a benzene ring having a substituting group being a acetyl group and a pyrazolo[4,3d]pyrimidin having a substituting group being a C1~C6 alkyl group;

Ra is one selected from a group consisting of a hydrogen group, a C1~C5 alkyl group and a C1~C5 hydroxyalkyl group;

RX substituent contains a carboxylic group donated from one of a Statin derivative, a Vitamin, a γ-polyglutamic acid derivative and a sodium CMC; and $RX^-$ substituent is an anion of the carboxylic group carrying a negative charge.

7. According to example 1, R1 is one selected from a group consisting of a benzene ring having a substituting group being a C1~C5 alkoxy group, a benzene ring having a substituting group being a sulfonyl group and a imidazo[5,1-f][1,2,4]triazin having a substituting group being a C1~C6 alkyl group;

Ra is one selected from a group consisting of a hydrogen group, a C1~C5 alkyl group and a C1~C5 hydroxyalkyl group;

RX substituent contains a carboxylic group donated from one of a Statin derivative, a Vitamin, a γ-polyglutamic acid derivative and a sodium CMC; and RX– substituent is an anion of the carboxylic group carrying a negative charge.

8. According to example 1, R1 is one selected from a group consisting of a benzene ring having a substituting group being a C1~C5 alkoxy group, a benzene ring having a substituting group being a acetyl group and a imidazo[5,1-f][1,2,4]triazin having a substituting group being a C1~C6 alkyl group;

Ra is one selected from a group consisting of a hydrogen group, a C1~C5 alkyl group and a C1~C5 hydroxyalkyl group;

RX substituent contains a carboxylic group donated from one of a Statin derivative, a Vitamin, a γ-polyglutamic acid derivative and a sodium CMC; and RX– substituent is an anion of the carboxylic group carrying a negative charge.

9. A pharmaceutical composition includes a pharmaceutically acceptable carrier; and an effective amount of a mixture of a Sildenafil-analogues complex salt of formula (I) and a carboxylic group donated from one of a Statin derivative, a Vitamin, a γ-polyglutamic acid derivative and a sodium CMC.

10. According to example 9, the Statin derivative is one selected from a group consisting of Atorvastatin, Cerivastatin, Fluvastatin, Lovastatin, Mevastatin, Pravastatin, Rosuvastatin and Simvastatin.

11. According to example 9, the γ-polyglutamic acid derivative is one selected from a group consisting of an alginate sodium, a γ-polyglutamic acid, a sodium polyglutamate, a GLT and a calcium polyglutamate-alginate sodium.

12. According to example 9, the Sildenafil-analogues is one selected from a group consisting of Sildenafil, Homosildenafil, Hydroxyhomosildenafil, Desmethylsildenafil, Acetidenafil and Vardenafil.

13. According to example 9, the Vitamin is one selected from a group consisting of Retinoic Acid, Ascorbic acid, Folic acid, Gamma-Linolenic Acid, Nicotinic Acid and Pantothenic acid.

14. A pharmaceutical composition of Sildenafil-analogues complex salt includes: a pharmaceutically acceptable carrier; and an effective amount of a Sildenafil-analogues complex salt of formula (I) and a carboxylic group donated from one of a Statin derivative, a Vitamin, a γ-polyglutamic acid derivative and a sodium CMC.

15. According to example 14, Sildenafil-analogues complex salt is one selected from a group consisting of Sildenafil, Homosildenafil, Hydroxyhomosildenafil, Desmethylsildenafil, Acetidenafil and Vardenafil.

16. According to example 14, the Statin derivative is one selected from a group consisting of Atorvastatin, Cerivastatin, Fluvastatin, Lovastatin, Mevastatin, Pravastatin, Rosuvastatin and Simvastatin.

17. According to example 14, the γ-polyglutamic acid derivative is one selected from a group consisting of an alginate sodium, a γ-polyglutamic acid, a sodium polyglutamate, a GLT and a calcium polyglutamate-alginate sodium.

18. According to example 14, the Vitamin is one selected from a group consisting of Retinoic Acid, Ascorbic acid, Folic acid, Gamma-Linolenic Acid, Nicotinic Acid and Pantothenic acid.

19. A pharmaceutical composition for lowering blood lipids includes: a pharmaceutically acceptable carrier; and an effective amount of a mixture of a Sildenafil-analogues complex salt of formula (I) and a carboxylic group donated from one of a Statin derivative, a Vitamin, a γ-polyglutamic acid derivative and a sodium CMC.

20. According to example 19, Sildenafil-analogues complex salt is one selected from a group consisting of Sildenafil, Homosildenafil, Hydroxyhomosildenafil, Desmethylsildenafil, Acetidenafil and Vardenafil.

21. According to example 19, the Statin derivative is one selected from a group consisting of Atorvastatin, Cerivastatin, Fluvastatin, Lovastatin, Mevastatin, Pravastatin, Rosuvastatin and Simvastatin.

22. According to example 19, the γ-polyglutamic acid derivative is one selected from a group consisting of an alginate sodium, a γ-polyglutamic acid, a sodium polyglutamate, a GLT and a calcium polyglutamate-alginate sodium.

23. According to example 19, the Vitamin is one selected from a group consisting of Retinoic Acid, Ascorbic acid, Folic acid, Gamma-Linolenic Acid, Nicotinic Acid and Pantothenic acid.

24. A pharmaceutical composition for pulmonary hypertension includes: a pharmaceutically acceptable carrier; and an effective amount of a mixture of a Sildenafil-analogues complex salt of formula (I) and a carboxylic group donated from one of a Statin derivative, a Vitamin, a γ-polyglutamic acid derivative and a sodium CMC.

25. According to example 24, Sildenafil-analogues complex salt is one selected from a group consisting of Sildenafil, Homosildenafil, Hydroxyhomosildenafil, Desmethylsildenafil, Acetidenafil and Vardenafil.

26. According to example 24, the Statin derivative is one selected from a group consisting of Atorvastatin, Cerivastatin, Fluvastatin, Lovastatin, Mevastatin, Pravastatin, Rosuvastatin and Simvastatin.

27. According to example 24, the Vitamin is one selected from a group consisting of Retinoic Acid, Ascorbic acid, Folic acid, Gamma-Linolenic Acid, Nicotinic Acid and Pantothenic acid.

28. According to example 24, the γ-polyglutamic acid derivative is one selected from a group consisting of an alginate sodium, a γ-polyglutamic acid, a sodium polyglutamate, a GLT and a calcium polyglutamate-alginate sodium.

29. A pharmaceutical composition for pulmonary fibrosis includes: a pharmaceutically acceptable carrier; and an effective amount of a mixture of a Sildenafil-analogues complex salt of formula (I) and a carboxylic group donated from one of a Statin derivative, a Vitamin, a γ-polyglutamic acid derivative and a sodium CMC.

30. According to example 29, Sildenafil-analogues complex salt is one selected from a group consisting of Sildenafil, Homosildenafil, Hydroxyhomosildenafil, Desmethylsildenafil, Acetidenafil and Vardenafil.

31. According to example 29, the Statin derivative is one selected from a group consisting of Atorvastatin, Cerivastatin, Fluvastatin, Lovastatin, Mevastatin, Pravastatin, Rosuvastatin and Simvastatin.

32. According to example 29, the γ-polyglutamic acid derivative is one selected from a group consisting of an alginate sodium, a γ-polyglutamic acid, a sodium polyglutamate, a GLT and a calcium polyglutamate-alginate sodium.

33. According to example 29, the Vitamin is one selected from a group consisting of Retinoic Acid, Ascorbic acid, Folic acid, Gamma-Linolenic Acid, Nicotinic Acid and Pantothenic acid.

34. A complex salt includes a structure of $$\text{Ra—N} \overbrace{\phantom{XXXX}}^{R_1} \overset{\text{(N)}}{\underset{H}{\big|}}_n RX^+ \qquad \text{formula (III)}$$

an effective amount of a complex salt of formula (III), wherein $R_1$ is one selected from a group consisting of a benzene ring having a substituting group being a C1~C5 alkoxy group, a benzene ring having a substituting group being one of a sulfonyl group and an acetyl group, a pyrazolo[4,3d]pyrimidin having a substituting group being one of a C1~C6 alkoxy group and a C1~C6 alkyl group and an imidazo[5,14][1,2,4] triazin having a substituting group being one of a C1~C6 alkoxy group and a C1~C6 alkyl group;

$R_a$ is one selected from a group consisting of a hydrogen group, a halogen atom, an amino group, a nitro group, a C1~C5 alkyl group and a C1~C5 hydroxyalkyl group; and RX contains a carboxylic group donated from a group consisting of a mineral acid, an organic acid, a Statin derivative, a Vitamin, a γ-polyglutamic acid derivative and sodium CMC, wherein $RX^-$ is an anion of the carboxylic group carrying a negative charge; and (N) substituting group is one selected from a group consisting of amine, C3~C8 cyclic amines and heterocyclic N—H groups;

n is an integer from 0 to 5; and a pharmaceutically acceptable carrier.

35. According to example 34, RX is a Statin derivative being one selected from a group consisting of Atorvastatin, Cerivastatin, Fluvastatin, Lovastatin, Mevastatin, Pravastatin, Rosuvastatin and Simvastatin.

36. According to example 34, RX is the γ-polyglutamic acid derivative being one selected from a group consisting of an alginate sodium, a γ-polyglutamic acid, a sodium polyglutamate, a GLT and a calcium polyglutamate-alginate sodium.

37. According to example 34, RX is the Vitamin being one selected from a group consisting of Retinoic Acid, Ascorbic acid, Folic acid, Gamma-Linolenic Acid, Nicotinic Acid and Pantothenic acid.

38. A pharmaceutical composition includes:

an effective amount of Udenafil-analogues complex salt of formula (III) includes: a carboxylic group donated from one of a Statin derivative, a Vitamin, a γ-polyglutamic acid derivative and sodium CMC.

39. According to example 38, Udenafil-analogues is Udenafil.

40. According to example 38, the γ-polyglutamic acid derivative being one selected from a group consisting of an alginate sodium, a γ-polyglutamic acid, a sodium polyglutamate, a GLT and a calcium polyglutamate-alginate sodium.

41. According to example 38, the Statin derivative is one selected from a group consisting of Atorvastatin, Cerivastatin, Fluvastatin, Lovastatin, Mevastatin, Pravastatin, Rosuvastatin and Simvastatin.

42. According to example 38, the Vitamin is one selected from a group consisting of Retinoic Acid, Ascorbic acid, Folic acid, Gamma-Linolenic Acid, Nicotinic Acid and Pantothenic acid.

43. A pharmaceutical composition of Udenafil-analogues complex salt includes: a pharmaceutically acceptable carrier; and an effective amount of a Udenafil-analogues complex salt of formula (III) and a carboxylic group donated from one of a Statin derivative, a Vitamin, a γ-polyglutamic acid derivative and a sodium CMC.

44. According to example 43, Sildenafil-analogues complex salt is one selected from a group consisting of Sildenafil, Homosildenafil, Hydroxyhomosildenafil, Desmethylsildenafil, Acetidenafil and Vardenafil.

45. According to example 43, the Statin derivative is one selected from a group consisting of Atorvastatin, Cerivastatin, Fluvastatin, Lovastatin, Mevastatin, Pravastatin, Rosuvastatin and Simvastatin.

46. According to example 43, the γ-polyglutamic acid derivative is one selected from a group consisting of an alginate sodium, a γ-polyglutamic acid, a sodium polyglutamate, a GLT and a calcium polyglutamate-alginate sodium.

47. According to example 43, the Vitamin is one selected from a group consisting of Retinoic Acid, Ascorbic acid, Folic acid, Gamma-Linolenic Acid, Nicotinic Acid and Pantothenic acid.

48. A pharmaceutical composition for lowering blood lipids includes: a carboxylic group donated from one of a Statin derivative, a Vitamin, a γ-polyglutamic acid derivative and sodium CMC.

49. According to example 48, Udenafil-analogues is Udenafil.

50. According to example 48, the Statin derivative is one selected from a group consisting of Atorvastatin, Cerivastatin, Fluvastatin, Lovastatin, Mevastatin, Pravastatin, Rosuvastatin and Simvastatin.

51. According to example 48, the γ-polyglutamic acid derivative is one selected from a group consisting of an alginate sodium, a γ-polyglutamic acid, a sodium polyglutamate, a GLT and a calcium polyglutamate-alginate sodium.

52. According to example 48, the Vitamin is one selected from a group consisting of Retinoic Acid, Ascorbic acid, Folic acid, Gamma-Linolenic Acid, Nicotinic Acid and Pantothenic acid.

53. A pharmaceutical composition for pulmonary hypertension includes: a pharmaceutically acceptable carrier; and an effective amount of a Udenafil-analogues complex salt of formula (III) and a carboxylic group donated from one of a Statin derivative, a Vitamin, a γ-polyglutamic acid derivative and a sodium CMC.

54. According to example 53, Udenafil-analogues is Udenafil.

55. According to example 53, the Statin derivative is one selected from a group consisting of Atorvastatin, Cerivastatin, Fluvastatin, Lovastatin, Mevastatin, Pravastatin, Rosuvastatin and Simvastatin.

56. According to example 53, the γ-polyglutamic acid derivative is one selected from a group consisting of an alginate sodium, a γ-polyglutamic acid, a sodium polyglutamate, a GLT and a calcium polyglutamate-alginate sodium.

57. According to example 53, the Vitamin is one selected from a group consisting of Retinoic Acid, Ascorbic acid, Folic acid, Gamma-Linolenic Acid, Nicotinic Acid and Pantothenic acid.

58. A pharmaceutical composition for pulmonary fibrosis includes: a pharmaceutically acceptable carrier; and an effective amount of a Udenafil-analogues complex salt of formula (III) and a carboxylic group donated from one of a Statin derivative, a Vitamin, a γ-polyglutamic acid derivative and a sodium CMC.

59. According to example 58, Udenafil-analogues is Udenafil.

60. According to example 58, the Statin derivative is one selected from a group consisting of Atorvastatin, Cerivastatin, Fluvastatin, Lovastatin, Mevastatin, Pravastatin, Rosuvastatin and Simvastatin.

61. According to example 58, the γ-polyglutamic acid derivative is one selected from a group consisting of an alginate sodium, a γ-polyglutamic acid, a sodium polyglutamate, a GLT and a calcium polyglutamate-alginate sodium.

62. According to example 58, the Vitamin is one selected from a group consisting of Retinoic Acid, Ascorbic acid, Folic acid, Gamma-Linolenic Acid, Nicotinic Acid and Pantothenic acid.

REFERENCES

1. Wu B N, Lin R J, Lo Y C, Shen K P, Wang C C, Lin Y T, Chen I J. KMUP-1, a xanthine derivative, induces relaxation of guinea-pig isolated trachea: the role of the epithelium, cyclic nucleotides and K⁺ channels. Br J Pharmacol 2004; 142(7): 1105-1114.
2. Lin R J, Wu B N, Lo Y C, Shen K P, Lin Y T, Huang C H, Chen I J. KMUP-1 relaxes rabbit corpus cavernosum smooth muscle in vitro and in vivo: involvement of cyclic GMP and K(+) channels Br J. Pharmacol. 2002 March; 135(5): 1159-1166.

What is claimed is:
1. A complex salt, comprising a structure of formula (I)

wherein
R₁ is one of:
a benzene ring having substituting groups of a C1~C5 alkoxy group, an acetyl group and a pyrazolo[4,3d]pyrimidin having a substituting group being one of a C1~C6 alkyl group; and
a benzene ring having substituting groups of a C1~C5 alkoxy group, a sulfonyl group and an imidazo[5,1-f][1,2,4]triazin having a substituting group being one of a C1~C6 alkoxy group and a C1~C6 alkyl group;
$R_a$ is one selected from a group consisting of a hydrogen group, a halogen atom, an amino group, a nitro group, a C1~C5 alkyl group and a C1~C5 hydroxyalkyl group;
RX contains a carboxylic group donated from a group consisting of a mineral acid, an organic acid, a Statin derivative, a Vitamin, a γ-polyglutamic acid derivative and sodium CMC, wherein RX⁻ is an anion of the carboxylic group carrying a negative charge; and
halogen atom is one selected from a group consisting of a fluorine, a chlorine, a bromine and an iodine.

2. A complex salt as claimed in claim 1, wherein RX is a Statin derivative being one selected from a group consisting of Atorvastatin, Cerivastatin, Fluvastatin, Lovastatin, Mevastatin, Pravastatin, Rosuvastatin and Simvastatin.

3. A complex salt as claimed in claim 1, wherein RX is the γ-polyglutamic acid derivative being one selected from a group consisting of an alginate sodium, a γ-polyglutamic acid, a sodium polyglutamate, a GLT and a calcium polyglutamate-alginate sodium.

4. A pharmaceutical composition, comprising:
an effective amount of a complex salt of formula (I)

wherein
R₁ is one of:
a benzene ring having substituting groups of a C1~C5 alkoxy group, an acetyl group and a pyrazolo[4,3d]pyrimidin having a substituting group being one of a C1~C6 alkoxy group and a C1~C6 alkyl group; and
a benzene ring having substituting groups of a C1~C5 alkoxy group, a sulfonyl group and an and an imidazo [5,1-f][1,2,4]triazin having a substituting group being one of a C1~C6 alkoxy group and a C1~C6 alkyl group;
R$_a$ is one selected from a group consisting of a hydrogen group, a halogen atom, an amino group, a nitro group, a C1~C5 alkyl group and a C1~C5 hydroxyalkyl group; and
RX contains a carboxylic group donated from a group consisting of a mineral acid, an organic acid, a Statin derivative, a Vitamin, a γ-polyglutamic acid derivative and sodium CMC, wherein RX⁻ is an anion of the carboxylic group carrying a negative charge; and
a pharmaceutically acceptable carrier.

5. A pharmaceutical composition as claimed in claim 4, wherein the Statin derivative is one selected from a group consisting of Atorvastatin, Cerivastatin, Fluvastatin, Lovastatin, Mevastatin, Pravastatin, Rosuvastatin and Simvastatin.

6. A pharmaceutical composition as claimed in claim 4, wherein the γ-polyglutamic acid derivative is one selected from a group consisting of an alginate sodium, a γ-polyglutamic acid, a sodium polyglutamate, a GLT, a calcium polyglutamate-alginate sodium.

7. A pharmaceutical composition as claimed in claim 4, wherein the complex salt is a Sildenafil-analogue being one of Acetidenafil, and Vardenafil.

8. A pharmaceutical composition comprising:

formula (III)

an effective amount of a complex salt of formula (III), wherein
R₁ is a benzene ring having substituting groups being a C1~C5 alkoxy group, a sulfonyl group and a pyrazolo [4,3d]pyrimidin having a substituting group being one of a C1~C6 alkoxy group and a C1~C6 alkyl group;
R$_a$ is one selected from a group consisting of a hydrogen group, a halogen atom, an amino group, a nitro group, a C1~C5 alkyl group and a C1~C5 hydroxyalkyl group; and
RX contains a carboxylic group donated from a group consisting of a mineral acid, an organic acid, a Statin derivative, a Vitamin, γ-polyglutamic acid derivative and sodium CMC, wherein RX⁻ is an anion of the carboxylic group carrying a negative charge; and
(N) substituting group is one selected from a group consisting of amine, C3~C8 cyclic amines and heterocyclic N—H groups;
n is an integer from 0 to 5; and
a pharmaceutically acceptable carrier.

9. A pharmaceutical composition as claimed in claim 8, wherein the Statin derivative is one selected from a group consisting of Atorvastatin, Cerivastatin, Fluvastatin, Lovastatin, Mevastatin, Pravastatin, Rosuvastatin and Simvastatin.

10. A pharmaceutical composition as claimed in claim 8, wherein the γ-polyglutamic acid derivative is one selected from a group consisting of an alginate sodium, a γ-polyglutamic acid, a sodium polyglutamate, a GLT and a calcium polyglutamate-alginate sodium.

* * * * *